United States Patent
Makdissi et al.

(10) Patent No.: US 12,157,010 B2
(45) Date of Patent: Dec. 3, 2024

(54) ENERGY HARVESTING MODULE WITH COMPACT-CONSTRUCTION PIEZOELECTRIC TRANSDUCER, IN PARTICULAR FOR POWERING A LEADLESS AUTONOMOUS CARDIACCAPSULE

(71) Applicant: CAIRDAC, Antony (FR)

(72) Inventors: Alaa Makdissi, Paris (FR); Willy Regnier, Longjumeau (FR); An Nguyen-Dinh, La Riche (FR); Julien Dohin, Vanves (FR); Steeven Vassal, Tours (FR); Thien Hoang, Tours (FR)

(73) Assignee: CAIRDAC, Antony (FR)

( * ) Notice: Subject to any disclaimer, the term of this patent is extended or adjusted under 35 U.S.C. 154(b) by 312 days.

(21) Appl. No.: 17/838,132

(22) Filed: Jun. 10, 2022

(65) Prior Publication Data

US 2023/0061434 A1   Mar. 2, 2023

(30) Foreign Application Priority Data

Aug. 25, 2021   (EP) .................................... 21315143

(51) Int. Cl.
*A61N 1/375*   (2006.01)
*A61N 1/372*   (2006.01)
(Continued)

(52) U.S. Cl.
CPC ....... *A61N 1/3785* (2013.01); *A61N 1/37205* (2013.01); *A61N 1/3756* (2013.01); *H02N 2/188* (2013.01); *H10N 30/306* (2023.02)

(58) Field of Classification Search
CPC ............. A61N 1/3785; A61N 1/37205; A61N 1/3756; A61N 1/362; H02N 2/188;
(Continued)

(56) References Cited

U.S. PATENT DOCUMENTS

| | | |
|---|---|---|
| 2006/0217776 A1* | 9/2006 | White ................. A61N 1/3785 607/35 |
| 2017/0077839 A1 | 3/2017 | Karami et al. |
| 2018/0185638 A1 | 7/2018 | Regnier |

FOREIGN PATENT DOCUMENTS

| | | |
|---|---|---|
| EP | 3693056 A1 | 8/2020 |
| WO | WO-2014116794 | 7/2014 |

* cited by examiner

*Primary Examiner* — Yingchuan Zhang
*Assistant Examiner* — Anh-Khoa N Dinh
(74) *Attorney, Agent, or Firm* — CRGO Global; Steven M. Greenberg

(57) ABSTRACT

An energy harvesting module includes a pendular unit with piezoelectric transducer elastically deformable in bending with a clamped end and a free end coupled to an inertial mass. The transducer includes at least one piezoelectric beam configured into two adjacent arms formed single-piece, with external and internal arms arranged side-by-side. The external arm has a clamped proximal end and a free distal end, and the internal arm has a free proximal end supporting the inertial mass, and a free distal end connected to the distal end of the adjacent external arm. An annular mount surrounds the beam at its proximal end and includes the clamp to which is fastened the proximal end of the external arm. The mount includes, in a central region in the vicinity of the clamp, a cavity inside which the inertial mass carried by the free proximal end of the internal arm can oscillate.

12 Claims, 11 Drawing Sheets

(51) Int. Cl.
*A61N 1/378* (2006.01)
*H02N 2/18* (2006.01)
*H10N 30/30* (2023.01)

(58) Field of Classification Search
CPC .......... H02N 2/181; H02N 2/186; H02N 2/18; H10N 30/306; H10N 30/2045; A44C 9/0053; H02J 50/001; H02J 50/005; H02J 50/10; H02J 7/007; H02K 11/049; H02K 11/05; H02K 35/02; H02K 7/02; H02K 7/116; H02K 7/1807; Y02E 60/16
See application file for complete search history.

ENERGY HARVESTING MODULE WITH COMPACT-CONSTRUCTION PIEZOELECTRIC TRANSDUCER, IN PARTICULAR FOR POWERING A LEADLESS AUTONOMOUS CARDIACCAPSULE

CROSS REFERENCE TO RELATED APPLICATIONS

This application claims priority under 35 U.S.C. § 119(a) to European patent application 21315143.4 filed on Aug. 25, 2021, the entire teachings of which are incorporated herein by reference.

BACKGROUND OF THE INVENTION

Field of the Invention

The present invention relates to energy harvesting devices, also called "harvesters" or "scavengers", which collect the mechanical energy resulting from various movements they undergo and convert this mechanical energy into electrical energy; and more particularly to the harvesting devices of the so-called "PEH" (Piezoelectric Energy Harvester) type, which use as a mechanical-electrical transducer an oscillating piezoelectric beam coupled to an inertial mobile mass.

Description of the Related Art

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limiting the invention, whose teachings can be applied to many other types of autonomous devices incorporating an energy harvester of the PEH type, whether these devices are implantable or not, medical or not.

In the field of medical implants, the recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage component. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of implantable medical devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a body of very small size able to be implanted at sites of difficult access or leaving little available space, such as the ventricle apex, the inner wall of the atrium, etc. Published request under the Patent Cooperation Treaty (PCT) WO 2019/001829 A1 by Cairdac, corresponding to U.S. Pat. No. 11,045,657 B2, as well as European patent EP 3,693,056 A1 and United States Patent Application Publication No. 2018/185638 A1 describe examples of such intracardiac leadless capsules.

The invention more particularly relates to capsules or similar implantable devices whose energy harvester is of the PEH type, i.e. using a Piezoelectric Transducer or "PZT" and an inertial pendular unit subjected to the external stresses described hereinabove. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, oscillates at a natural free oscillation frequency.

The mechanical energy of the oscillation is converted into electrical energy by a mechanical-electrical transducer producing an electrical signal. This mechanical-electrical transducer may be in particular a PZT that is cyclically stressed in bending so as to generate within its constituent material electrical charges that are collected at the surface of the component to be used by the self-powering system of the leadless capsule. The PZT is most often in the form of a beam clamped at one of its end and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage component. Such a PEH energy harvesting device is described in particular in U.S. Pat. No. 3,456,134 A to Ko and in the above-mentioned Published request under the PCT WO 2019/001829 A1 and '657 patent and United States Patent Application Publication No. 2006/217776 by White et al. describes a PEH with beams folded into two or three successive segments arranged in series, with a clamp at one end and an inertial mass at the opposite end.

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

The problem of the invention lies in the search for greater dimensional compactness of the PEH, while preserving its functional capacity to produce sufficient energy to power the circuits of the autonomous capsule and to charge the integrated buffer battery.

In particular, if it is desired to make leadless capsules that can be implanted in the atrium, the elongated tubular shape of the conventional capsules is not adapted, due to the much smaller volume of the atrial cavity with respect to the ventricle, and moreover the necessity to implant the capsule on a lateral wall of the atrium: an elongated capsule should then be implanted with its largest dimension more or less perpendicular to the superior vena cava, which in practice is not possible with this access route (in contrast, for a ventricular leadless capsule implanted in the bottom of the right ventricle, the apex is located in the continuation of the superior vena cava and the tricuspid valve, therefore does not pose any particular difficulty of implantation, and moreover the elongated shape of the capsule is not a problem due to the larger volume of the ventricular cavity).

It would be the same for an epicardial capsule, i.e. implanted at the external surface of the myocardium, for which it would be desirable to have a flat rather than elongated element.

The interest of an atrial leadless capsule is the possibility to implement a "dual chamber" pacing, for which it is necessary to have electrodes at the atrium to ensure the required functions of atrial detection and/or pacing.

The implantation of a conventional lead, provided with electrodes at the atrium and the ventricle and connected to a remote generator, does not pose particular difficulty. On the other hand, with the leadless technique, it is necessary to implant a first capsule in the ventricle and a second capsule in the atrium, the two capsules being provided with mutual communication means to ensure the required functions of the dual chamber pacing.

Reducing the capsule length is therefore an essential prerequisite for the making of an implantable atrial leadless capsule.

But if such a capsule is powered by a harvester of the PEH type, the presence of the PZT beam, which must be long enough to allow a sufficient travel to produce enough electrical charges to suitably power the circuits of the capsule, entails for the capsule a length form factor, which is the one typically found on almost all the capsules described by the state of the art, which have an elongated tube shape.

However, this problem of seeking greater compactness is not specific to the cardiac leadless capsules, atrial or other, but arises whenever it is desired to miniaturize a PEH system, whatever the intended application.

Generally, in a perspective of advanced miniaturization and design integration of a PEH, it is desirable to reduce the overall volume necessary for the oscillation of the PZT beam, which is a dead volume, in which it is not possible to place electrical, electronic or mechanical components, or which would make it possible to have a slightly larger battery providing an increased capacity.

In this same perspective, it would also be desirable that a same structure element can ensure several functions, in order to reduce the overall volume of the system, facilitate industrialization and reduce manufacturing costs.

BRIEF SUMMARY OF THE INVENTION

To solve the different problems and achieve the goals mentioned above, the invention proposes an energy harvesting module of the PEH type comprising, in a manner known per se, a pendular unit subjected to external stresses applied to the module, the pendular unit comprising a piezoelectric transducer extending, along a central axis corresponding to a direction of greater length of the piezoelectric transducer, from a distal end to an opposite proximal end, the transducer being elastically deformable in bending between a clamped end and a free end coupled to an inertial mass. The piezoelectric transducer is adapted to convert a mechanical energy produced by oscillations of the pendular unit into an oscillating electrical signal collected by surface electrodes of the piezoelectric transducer.

Characteristically, according to a first aspect of the invention: the piezoelectric transducer comprises two coplanar piezoelectric beams arranged side-by-side on either side of said central axis, each of the piezoelectric beams comprising adjacent external and internal arms, arranged side-by-side and formed single-piece; the external arm of each piezoelectric beam has a clamped proximal end and a free distal end; the internal arm of each piezoelectric beam has a free proximal end supporting the inertial mass, and a free distal end connected to the distal end of the adjacent external arm by a common junction; the inertial mass as well as the respective clamped proximal ends of the external arms of the two piezoelectric beams are arranged at the proximal end of the piezoelectric transducer; and the respective common junctions of the two piezoelectric beams are arranged at the distal end of the piezoelectric transducer. That way, the oscillations of the pendular unit produce respective displacements of the two internal arms in a first direction and, simultaneously, of the two external arms in a second, opposite direction.

According to various advantageous embodiments:
surface electrodes are provided on one at least of the external and internal arms of each piezoelectric beam, and the module further comprises a rectifier stage receiving on respective inputs the charges collected by the surface electrodes of each piezoelectric beam and outputting a rectified power supply signal;
surface electrodes are provided on either of the external and internal arms of each piezoelectric beam, the respective surface electrodes of the internal and external arms being adapted to collect charges of opposed polarities during a same deformation of the piezoelectric transducer;

the surface electrodes collecting charges of same polarity are directly connected to each other and coupled to a same respective input of the rectifier stage;

the piezoelectric beams are bimorphous beams comprising a conductive central core forming a common electrode and, for each internal and/or external arm, surface electrodes on a top and a bottom face;

the rectifier stage comprises a plurality of rectifier circuits associated with respective pairs of electrodes outputting charges of opposed polarities, and the outputs of the plurality of rectifier circuits are directly connected to each other;

the external and internal arms of each piezoelectric beam are parallel and/or rectilinear and/or are of same length for both piezoelectric beams;

the internal and external arms are of different lengths for the two respective piezoelectric beams;

the respective internal arms of the two piezoelectric beams are partially or fully merged into a single arm;

one at least of the piezoelectric beams carries at its free distal end an intermediate flyweight at the junction between the internal and external arms;

the two piezoelectric beams carry a common intermediate flyweight at the junction, and/or each carry independently their own flyweight at the junction.

According to a second aspect of the invention, the piezoelectric transducer comprises at least one piezoelectric beam configured as two adjacent arms formed single-piece, with an external arm and internal arm arranged side-by-side, the external arm having a clamped proximal end and a free distal end, and the internal arm having a free proximal end supporting the inertial mass, and a free distal end connected to the distal end of the external arm. The module further comprises around the central axis an annular mount that surrounds the piezoelectric beam at its proximal end and that comprises said clamp to which is fastened the proximal end of the external arm, the annular mount includes, in a central region in the vicinity of the clamp, a cavity inside which the inertial mass carried by the free proximal end of the internal arm can oscillate transversely to the central axis.

According to various advantageous embodiments:

the annular mount comprises a stroke limiter having inside the cavity stroke-limiting surfaces adapted to form a stop for the inertial mass in a configuration of maximum bending of the piezoelectric beam;

the inertial mass comprises stroke-limiting surfaces complementary of the facing stroke-limiting surfaces of the annular mount;

the mutual contact between the stroke-limiting surfaces of the annular mount and the stroke-limiting surfaces of the inertial mass is one of: a plane contact, a linear contact, or a cylindrical surface contact;

the stroke-limiting surfaces of the annular mount and/or of the inertial mass are coated with a flexible damping material, or made of a damping material;

the piezoelectric transducer comprises two coplanar piezoelectric beams arranged side-by-side, each of the piezoelectric beams comprising a so-called external arm and a so-called internal arm, wherein the proximal ends of the internal arms of the two piezoelectric beams support together the inertial mass, and the proximal ends of the external arms of the two piezoelectric beams are each connected to a respective clamp of the annular mount, the two clamps being located on either side of the inertial mass in the cavity;

the position of the center of gravity of the inertial mass is located inside the cavity of the annular mount;

in an axial direction of the beam in its longer dimension, the position of the center of gravity of the inertial mass is offset in the proximal direction with respect to the center of the annular mount cavity;

the piezoelectric beam carries at its free distal end an intermediate flyweight at the junction between the external arm and the internal arm; and/or the module further comprises, in the vicinity of the distal end of the piezoelectric beam, a stroke limiter adapted to form a stop for the intermediate flyweight in a configuration of maximum bending of the piezoelectric beam.

The invention has also for object an autonomous device housing, within a device body: an electronic unit; an energy harvesting module as described hereinabove, outputting an oscillating electric signal; a power management circuit, adapted to rectify and regulate the oscillating electric signal produced by the energy harvesting module, to output stabilized direct voltage or current; and an energy storage component for powering the electronic unit. Said stabilized direct voltage or current provided by the power management circuit is used to power the electronic unit and/or to charge the energy storage component of the autonomous device.

In particular, the autonomous device can be an active medical device of the implantable autonomous capsule type comprising a capsule body with an element for its anchoring to a wall of a patient's organ, the external stresses to which is subjected the pendular unit of the energy harvesting module being stresses applied to the capsule body under the effect of movements of said wall and/or blood flow rate variations in the surrounding environment.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of autonomous devices incorporating an energy harvester of the PEH type, whether these devices are implantable or not, medical or not.

Figure 1:
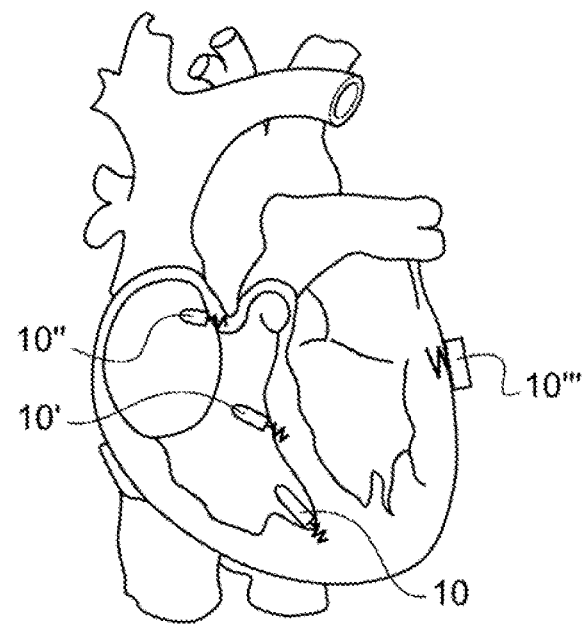
FIG. 1 illustrates medical devices of the leadless capsule type in their environment, with various examples of implantation sites in, on or near a patient's heart.

FIG. 1 shows various possibilities of implantation sites for a leadless capsule device in an application to cardiac pacing. Therefore, the capsule 10 is implanted inside a cavity of the myocardium (endocavitary implant), for example at the apex of the right ventricle. As an alternative, the capsule may also be implanted on the right interventricular septum, as in 10', or also on an atrial wall, as illustrated in 10". The device may also be an epicardial capsule placed on an external region of the myocardium, as illustrated in 10'''.

In any case, the leadless capsule is fixed to the heart wall by means of a protruding anchoring system intended to enter the heart tissue for the holding on the implantation site. Other anchoring systems can be used, and do not change in any way the implementation of the present invention.

Capsule 10 has the external form of an implant with an elongated tubular body 12 enclosing the various electronic and power supply circuits of the capsule, as well as an energy harvester with a pendular unit. The typical size of the known capsules is about 6 mm diameter for about 25 to 40 mm length.

Tubular body 12 has, at its front (distal) end 14, a protruding anchoring element, for example a helical screw 16, to hold the capsule on the implantation site. Other anchoring systems can be used, and do not change in any way the implementation of the present invention. The opposite (proximal) end 18 of capsule 10 is a free end, which is only provided with means (not shown) for the temporary connection to a guide-catheter or another implantation accessory used for implantation or explantation of the capsule, which is then detached from the latter.

Figure 2:
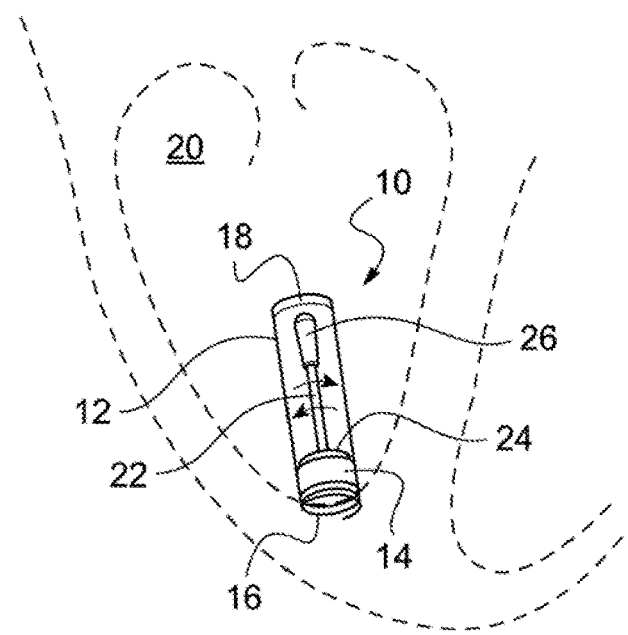
FIG. 2 illustrates a leadless capsule implanted in the bottom of the right ventricle of a patient.

In the example illustrated in FIG. 2, leadless capsule 10 is an endocavitary implant implanted into a cavity 20 of the myocardium, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16;

and/or blood flow rate variations in the environment surrounding the capsule, which produce oscillations of tubular body 12 at the rhythm of the heartbeats; and/or various vibrations transmitted by the heart tissues.

Figure 3:
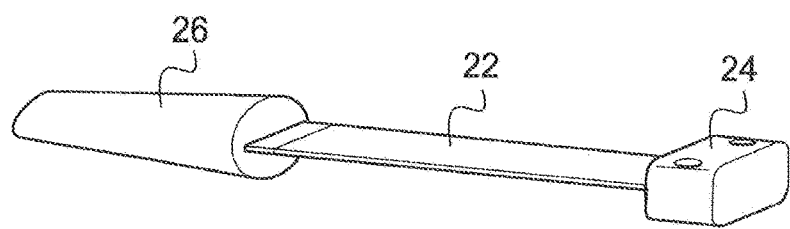
FIG. 3 shows in isolation a pendular unit of a known type, with a PZT in the form of an elongated beam clamped at one end and supporting an inertial mass at its opposite end.

The pendular unit, illustrated in isolation in FIG. 3, is consisted by a piezoelectric beam 22 clamped at one of its ends, at position 24, and whose opposite, free end is coupled to a mobile inertial mass 26. Piezoelectric beam 22 is an elastically deformable flexible beam that constitutes, with inertial mass 26, a pendular system of the mass-spring type. Due to its inertia, mass 26 subjects beam 22 to a deformation of the vibratory type on either side of a neutral or non-deformed position corresponding to a stable rest position in the absence of any stress. The typical minimum size of the PZT beams of the known devices of this type is of the order of 25 mm long for about 5 mm width.

Actually, as for its mechanical behavior, this unit may be equated to a "clamped/free beam" structure, having a natural oscillation frequency, which is herein the frequency at which the mass-spring system oscillates. It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 22 further performs, by piezoelectric effect, a mechanical-electrical transducer function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 4:
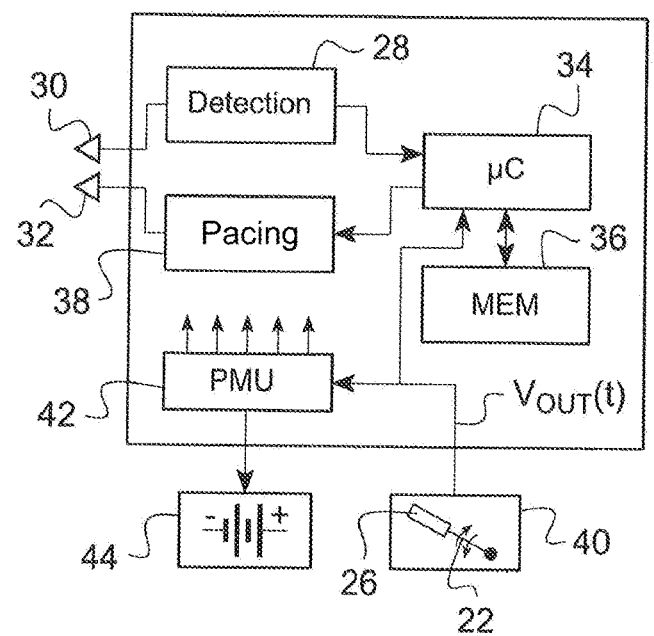
FIG. 4 schematically shows the main functional blocks of a leadless capsule.

FIG. 4 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to provide to the system of electrodes 30, 32 myocardial pacing pulses.

An energy harvesting circuit or PEH 40 is moreover provided, consisted by the pendular unit formed by piezoelectric beam 22 and inertial mass 26, described hereinabove with reference to FIGS. 2 and 3. As piezoelectric beam 22 also ensures a mechanical-electrical transducer function, it converts into electrical charges the mechanical stresses undergone and produces a variable electrical signal VOUT(t), which is an alternating signal oscillating at the natural oscillation frequency of the pendular beam 22/mass 26 unit, and at the rhythm of the successive beats of the myocardium to which the capsule is coupled.

The variable electrical signal VOUT(t) is sent to a power management circuit or PMU 42. PMU 42 rectifies and regulates the signal VOUT(t) so as to output a stabilized direct voltage or current for powering the various electronic circuits and charging the integrated battery 44.

On the other hand, the beam is advantageously a beam of the bimorphous type, i.e. capable of generating energy on its two faces when subjected to a deformation. Theses transduction properties are typical of a piezoelectric material, such as PZT ceramics or PMN-PT, barium titanate or lithium niobate mono-crystals.

Figure 5:
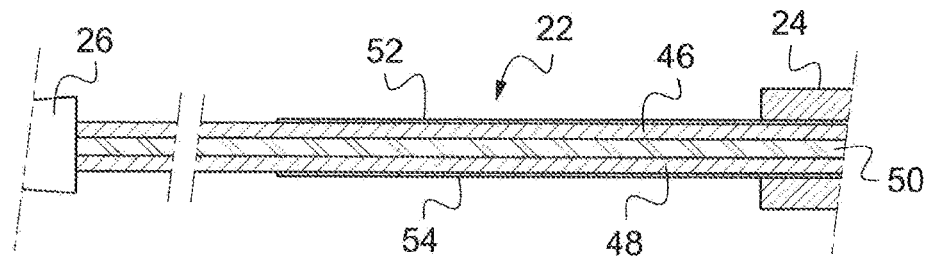
FIG. 5 is a cross-sectional view showing, with a deliberately exaggerated thickness scale, the structure of the different layers of a bimorphous PZT usable with the present invention.

FIG. 5 schematically illustrates, with a deliberately exaggerated thickness scale, the structure of the different layers of such a bimorphous PZT beam.

Bimorphous beam 22 comprises two layers 46, 48 of PZT ceramic material applied on each of the opposite faces of a central core or shim 50 made of a conductive material (or, as an alternative, of an isolating material, with contact bridges making it possible to shunt the internal electrodes of the piezoelectric layers). This bimorphous structure actually corresponds to the association of two monomorphous structures placed back-to-back, with sharing of the core supporting the PZT material. If core 50 is made of a conductive material, it is possible to collect the charges produced by the deformation of the PZT material as well between the conductive core 50 and a surface electrode 52, 54 of one and/or the other of the PZTs 46, 48, as between the two surface electrodes 52, 54 of the opposite faces of the beam, independently of the central core.

Figure 6:
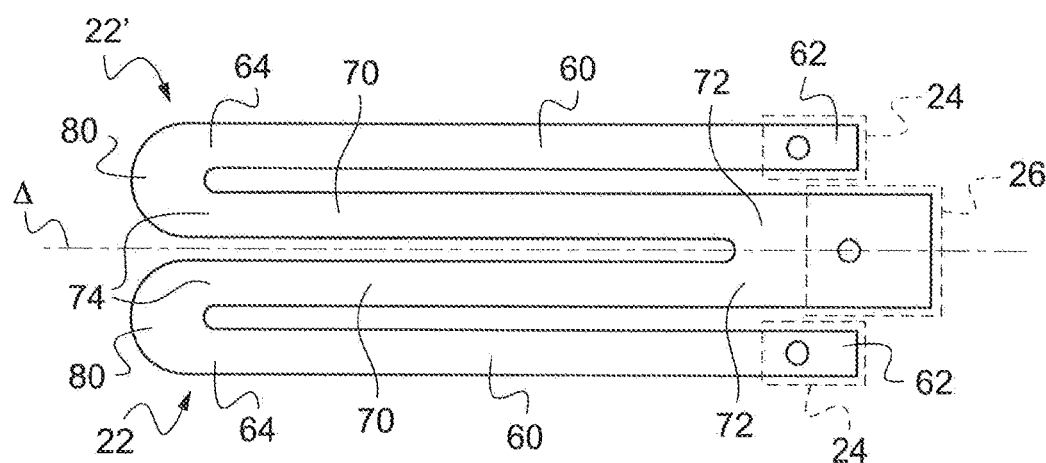
FIG. 6 is a top view of a PZT according to the invention, in the form of two beams arranged side-by-side, each with two internal and external parallel arms.

FIG. 6 is a top view of a PZT according to the invention, considered in isolation before the clamps are made and the inertial mass positioned.

Characteristically of the invention, this PZT is made of two coplanar piezoelectric beams 22, 22', arranged side-by-side on either side of a central axis corresponding to the direction of greater length of the PZT, from a distal end to an opposite proximal end. Both beams 22, 22' preferably extend symmetrically on either side of the central axis, as illustrated in the different embodiments described hereinafter.

Each of the two beams 22, 22' has a folded shape with two adjacent arms 60, 70, arranged side-by-side and formed single-piece. External arm 60 has its proximal end 62 clamped (clamp 24) and its distal end 64 free, whereas internal arm 70 has its proximal end 72 that is free to move and that supports inertial mass 26, and its distal end 74 that is free (here and in the following, the "proximal" side will be understood as that which is the closest to the beam clamp, and the "distal" side as the opposite side, which is the farthest from the clamp). Distal end 64 of external arm 60 and distal end 74 of internal arm 70 are connected to each other by a common junction 80.

The PZT consisted by the two beams 22, 22', each having the just-described internal and external arms, can be in particular made by laser-cut in a single piece of material.

Figure 28:
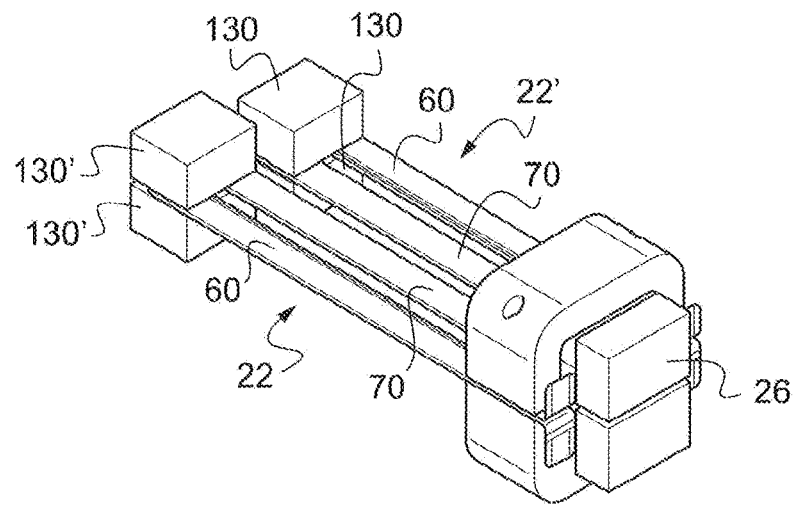
FIG. 28 is similar to FIG. 27, for an alternative in which the two beams of the PZT have different respective lengths.

Both beams 22, 22' may be symmetrical (as illustrated) or not, of same length (as illustrated) or not (FIG. 28 shows in particular an example in which the two beams 22, 22' have different lengths).

For each beam, external and internal arms 60, 70 may be approximately parallel (as illustrated) or not, have parallel edges (as illustrated) or not, and be of same length and/or width (as illustrated) or not.

As described in European patent application publication EP 3930014A1 by Cairdac, corresponding to United States Patent Application Publication No. 2021/408945, whose teachings are incorporated herein by way of reference, in order to reinforce the reliability of the PZT beams 22, 22', it is possible to give the latter, over all or part of their length, a trapezoidal shape in plan view, with a (linear or exponential) decrease of the width for a better distribution of the stresses along the beam, these stresses being stronger near and at clamp 24, and null at inertial mass 26. Moreover, the trapezoidal shape makes it possible to adjust the resonant frequency of the unit as a function of the trapezoidal geometry, while maximizing the amplitude of displacement of the mass due to the fact that the free end is narrower than the clamped end.

With the just-described configuration, each of the two beams 22, 22' has a dual cantilever corresponding to each of the two external and internal arms 60, 70, i.e.: a first cantilever for external arm 60 between clamp 24 at proximal end 62 and distal end 64 that is free to oscillate; and a second cantilever for internal arm 70 between distal end 74 connected to distal end 64 (mobile) of external arm 60 and proximal end 72 carrying inertial mass 26.

The oscillations of the pendular unit consisted by clamp 24, beam 22 and inertial mass 26 produce respective displacements of both arms 60, 70 in respective opposite directions (see FIG. 15 below, which shows, in elevation and cross-section, the respective opposite bending of these two arms).

From the point of view of the transducer overall bulk, this particular configuration made of two parallel arms allows for a significant reduction in the PZT overall length (considered in the longitudinal direction of axis) with respect to a conventional beam as that illustrated in FIG. 3, the gain in length being typically of at least 20 to 40%.

Above all, with this particular arrangement, the respective common junctions 80 of both piezoelectric beams 22, 22' are both located at the distal end of the piezoelectric transducer, whereas inertial mass 26 is located at the opposite, proximal end, of the piezoelectric transducer. That way, the PZT clamps 24 are brought on the same side (proximal side of the PZT) as inertial mass 26, whereas the opposite side (distal side of the PZT) does not include clamps 24 or inertial mass 26.

It will be noted that this configuration according to the invention is the reverse of the conventional configurations such as that illustrated in FIG. 3, where inertial mass 26 is located on one side of the PZT and the clamp on the opposite side.

The grouping together, according to the invention, of the clamps and the inertial mass in a same region of the PEH provides the latter with a significantly increased compactness, with no concessions on efficiency of the mechanical-electrical transduction by the PZT.

On the other hand, with the dual cantilever and the displacements of the two arms in opposite directions, the overall amplitude of the beam oscillation will be reduced with respect to a conventional PZT due to the fact that the respective strokes of each of the two arms 60, 70 add up each other in absolute value but are in opposite directions. This also makes it possible to significantly reduce the volume necessary for the travel of the pendular unit with respect to a conventional configuration, with a correlative reduction in dead volume, which in practice is a wasted space that cannot be used for accommodating circuit components or housing a larger battery.

Figure 7:
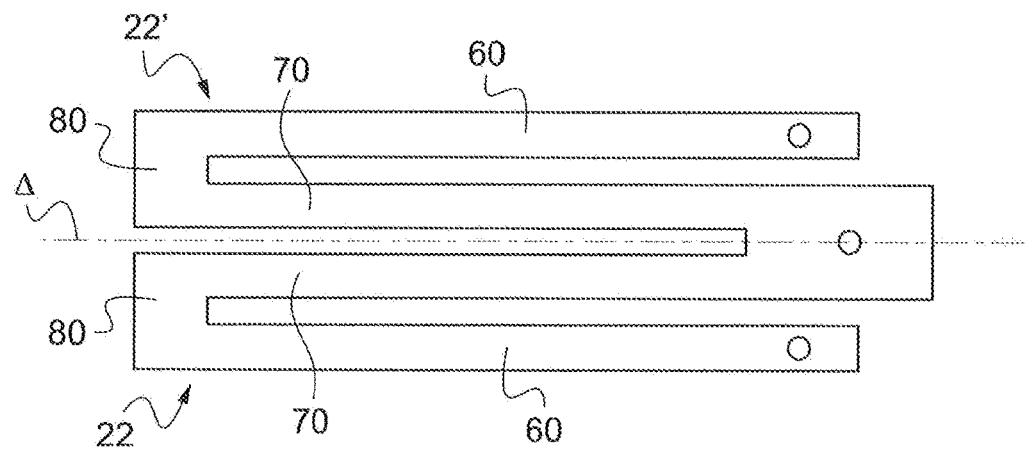
FIG. 7 is similar to FIG. 6, for an alternative with a non-round curvature at the junction between the two internal and external arms.

FIG. 7 illustrates an alternative of FIG. 6 in which junction 80 between external and internal arms 60, 70 is not round, but rectangular. The round configuration of FIG. 6 however allows a better distribution of the stresses at junction 80 between the two arms, these constraints resulting from the fact that these two arms bend in opposite directions even though they are formed single-piece.

Figure 8:
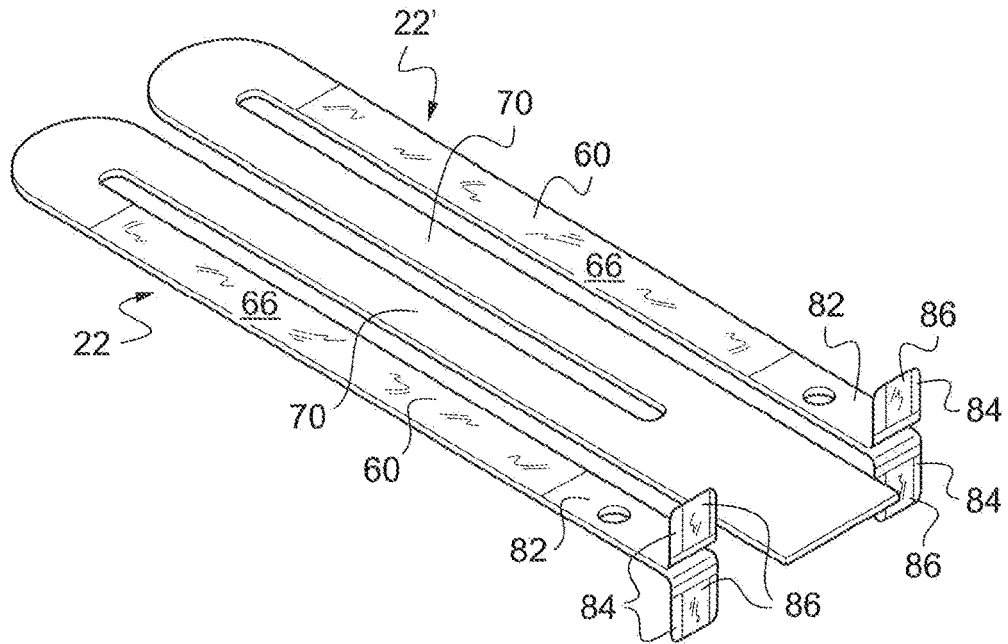
FIG. 8 is a perspective view of the PZT of FIG. 6, provided with surface electrodes on each of the bottom and top faces of each external arm.
Figure 9:
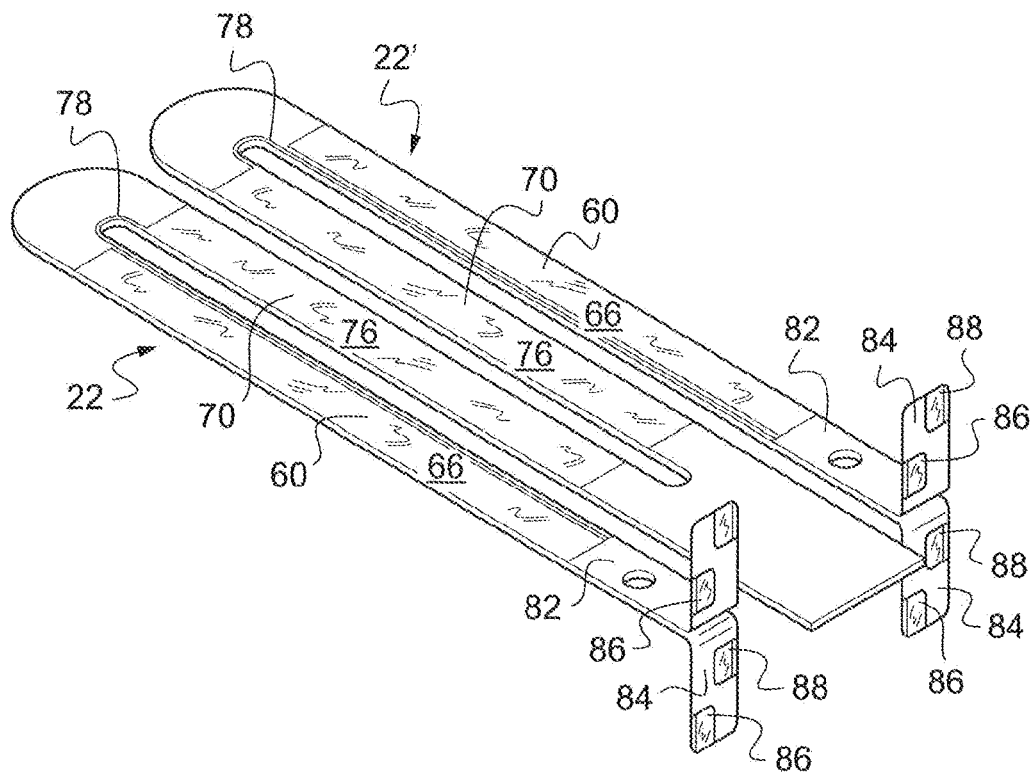
FIG. 9 is similar to FIG. 8, for an alternative in which the external as well as internal arms are provided with surface electrodes.

Collection of the electrical charges produced by the bending of the arms during oscillations is ensured by a system of electrodes illustrated in the perspective views of FIGS. 8 and 9.

In FIG. 8 is shown an embodiment in which external arms 60 of each beam 22, 22' are provided with surface electrodes 66 extending over the major part of the arm length. These electrodes are for example made by depositing gold, cupper, platinum or any other conductive material, and are electrically connected at the proximal end of the arm to a flexible circuit or flex 82 extended by a raised free part 84 carrying a connection area or pad 86 electrically connected to electrode 66 and allowing the transfer of the electrical charges produced by the latter to a power supply circuit.

If the beam used is a bimorphous beam such as that described hereinabove in relation with FIG. 5, the opposite bottom face (not visible in the Figure) of external arm 60 is provided with a similar electrode, connected to another pad 86 at the proximal end of the same arm. The facing electrodes on opposite faces then collect charges of opposite signs, conducted to the corresponding pad 86. The central core of the bimorphous beam (referenced 50 in FIG. 5) may also include an electrical connection to a corresponding pad used as a "neutral" electrical reference potential.

With a bimorphous beam, the configuration of FIG. 8 thus includes a total of four electrodes 66 (two electrodes on each side of each external arm 60), four flex 82 and four pads 86.

Moreover, as described in the above-mentioned EP 3 930 014 A1 and US 2021/408945 A1, it is possible to split the surface electrodes, or some of them, on the top face and/or the bottom face of the beam, into two or more sub-electrodes electrically insulated from each other. These split sub-electrodes, which may be symmetrical or not with respect to a central longitudinal axis of the beam, are then each connected to a respective distinct pad for the contact and link with downstream rectifier stages.

FIG. 9 illustrates another embodiment in which, in addition to electrodes 66 on external arms 60 of FIG. 8, the PZT also includes electrodes 76 on internal arms 70.

Insofar as internal arms 76 move in a direction opposite to that of external arms 60, the respective surface electrodes of the internal and external arms will collect charges of opposite signs during a same deformation of the PZT (positive charge on electrodes 66 and negative charge on electrodes 76, and vice versa at the following half-oscillation). As it is not possible for this reason to connect electrodes 76 and 66 in series, each electrode 76 is connected to flex 82 by a conductor 78 that runs along external arm 60 by being electrically insulated from electrode 66, in order to ensure a connection by a pad 88 on the raised free end part 84 of the flex, in the vicinity of pads 86 connected to electrodes 66 of external arms 60.

With a similar electrode configuration on the inner face (not visible in the Figure), the arrangement obtained includes eight electrodes 66, 76, four flex 82 and eight pads 86, 88.

Figure 10:
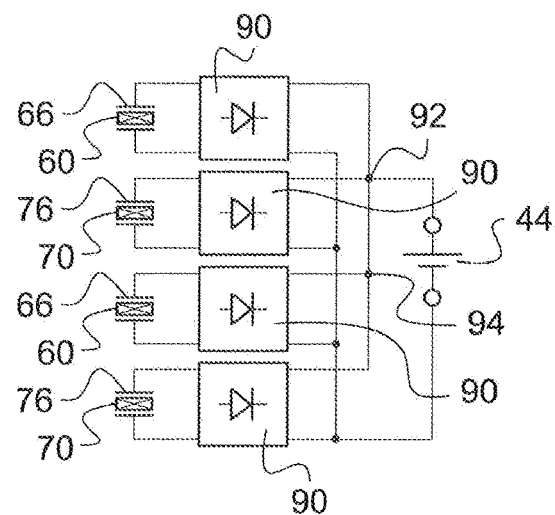
FIG. 10 is a simplified electric diagram showing the way to couple the different surface electrodes of the PZT of FIG. 9 to rectifiers, in order to output a charging current for a buffer battery.

FIG. 10 is a simplified electric diagram showing the way to couple to each other the various electrodes of the configuration of FIG. 9 in such a way that the PEH outputs a power supply and/or charging current for a buffer battery.

Each couple of electrodes at the bottom/top face of each of the arms 60 or 70 is connected to a respective rectifier circuit 90, for example a Full Wave Bridge Rectifier (FBR), for example a diode bridge (Graetz bridge), or a MOSFET-based negative voltage converter (NVC) or another similar circuit. The respective outputs of rectifier circuits 90 are connected to a common positive terminal 92 and to a common negative terminal 94 providing between each other a charging current applied to buffer battery 44. Rectifier circuits 90 may possibly be made with compounds arranged directly on flex 84 and connected to the respective pads 86, 88.

Advantageously, the corresponding outputs (positive or negative) of rectifiers 90 are directly connected to each other, without intermediate coupling.

As an alternative, it is also possible to connect directly to each other the various surface electrodes collecting charges of same polarity, these electrodes being then coupled to a same respective input of a common rectifier stage, all the currents generated by the displacement of the charges of same sign being added to be provided to the battery after rectification.

Figure 11:
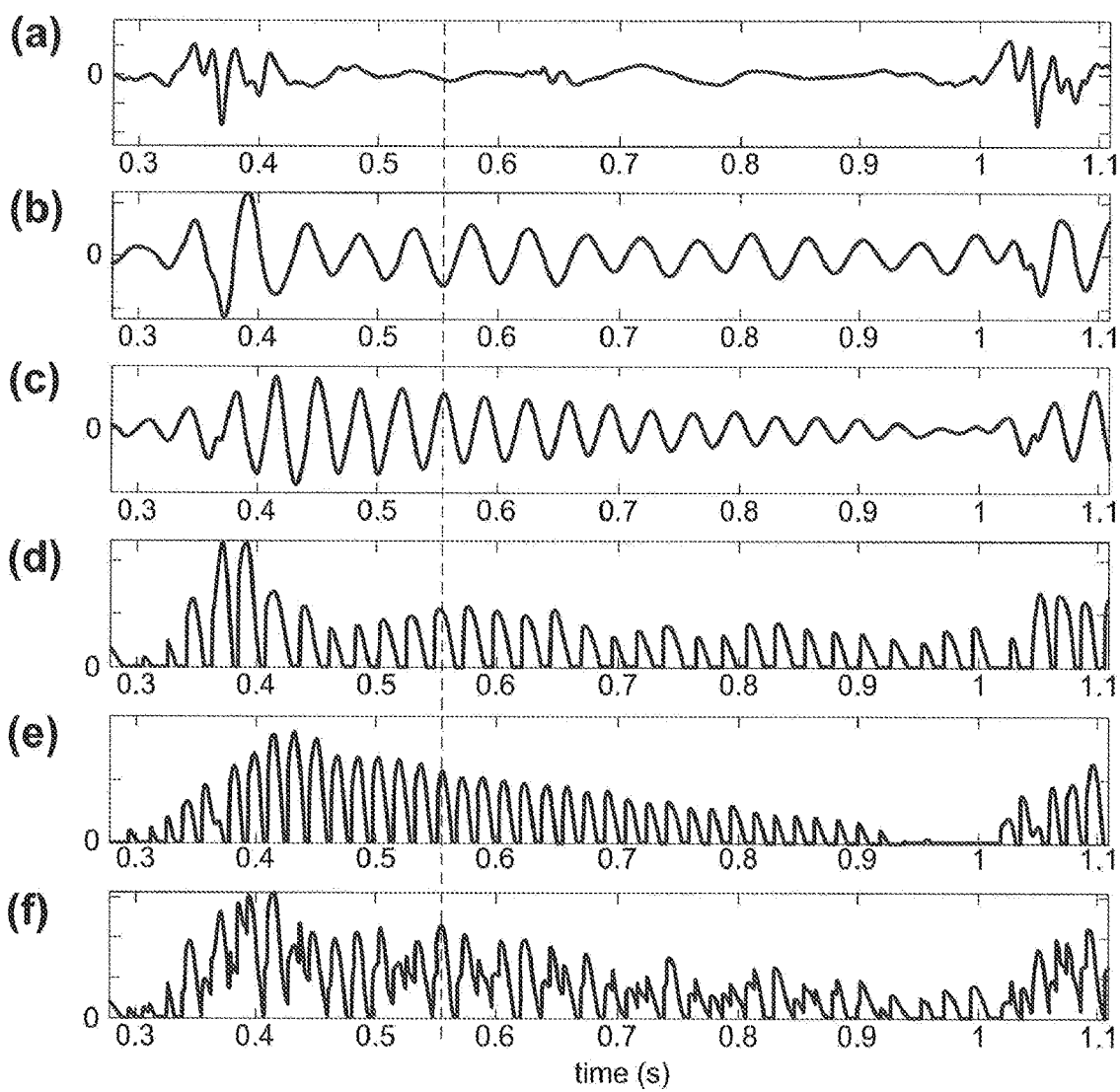
FIG. 11 shows a series of chronograms showing the instantaneous variations of the PZT acceleration and the various electrical signals collected by the electrodes before and after rectification and mutual coupling.

FIG. 11 is a series of chronograms showing:

(a) the instantaneous variations of the PZT acceleration;

(b) the current generated by a pair of top/bottom electrodes of one of the external arms 60;

(c) the current generated by a pair of top/bottom electrodes of one of the internal arms 70;

(d) the current (b), after full-wave rectification by a circuit 90;

(e) the current (c), after full-wave rectification by a circuit 90; and (f) the total current resulting from the addition of the currents (b) and (e), injected into the buffer battery 44 for charging the latter.

Figure 12:
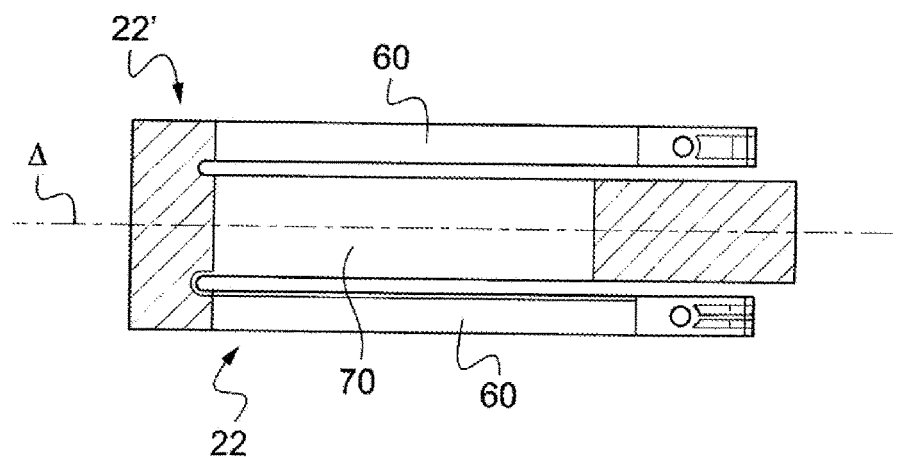
FIG. 12 illustrates an alternative of the PZT of the invention, in which the two internal arms are connected into a single arm common to the two beams.

FIG. 12 illustrates an alternative embodiment of the PZT described hereinabove in relation with FIGS. 6 and 7, in which the two internal arms 70 are merged into a single arm over their whole length (as an alternative, they may be merged over only part of their length). This alternative provides in particular the PZT with a higher stiffness at the place where stresses are concentrated during the pendular unit oscillations. As regards the electrode configuration, the central internal arm 70 carries a single electrode on each of its top and bottom faces, and each of the two external arms 60 carries an electrode on each of its top and bottom faces. In this case, a unit is obtained, which has a total of six electrodes, with six pads and four flex.

Figure 13:
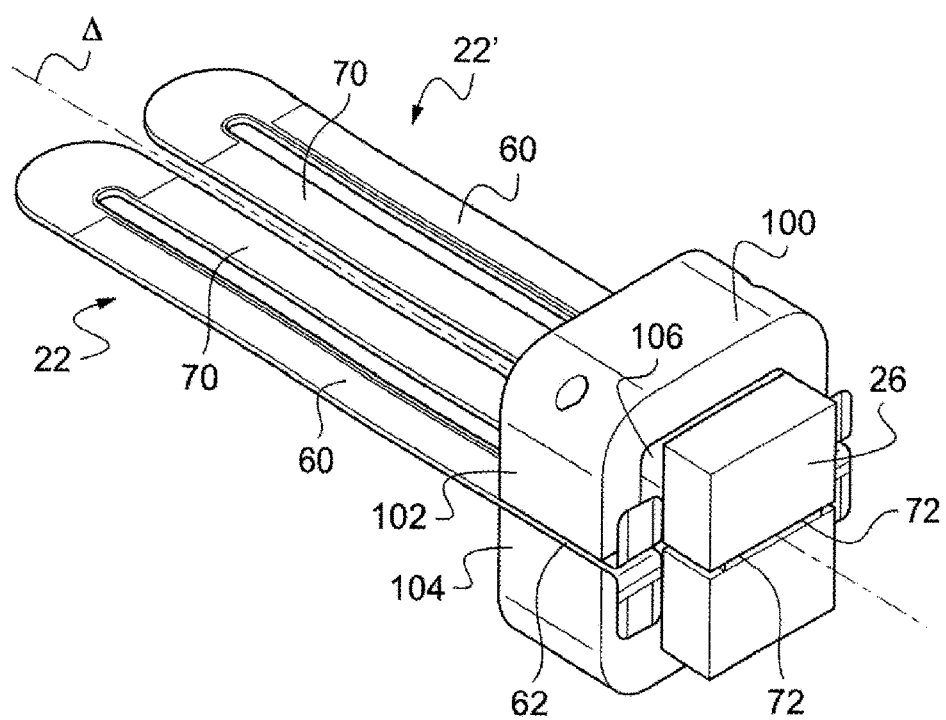
FIG. 13 is a perspective view showing the PZT of FIG. 9, equipped with an end inertial mass and attached to a mount that defines the clamps of the beams and further ensure a stroke-limitation function.

FIG. 13 illustrates the PZT according to the invention, as illustrated in particular in FIGS. 6 and 9, in a complete configuration of the pendular unit, with the clamps and the inertial mass mounted.

The clamp, at proximal ends 62 of each external arm 60, is made through a mount 100, which surrounds the PZT at its proximal end and which comprises clamps 24 to which are fastened proximal ends 62 of external arms 60. In the example illustrated, this mount is consisted of two distinct parts 102, 104 assembled in such a way as to sandwich proximal ends 62 of external arms 60, to form clamps 24 of the two PZT beams 22, 22' at this place.

Inertial mass 26 is mounted at proximal end 72 of internal arms 70, and has the possibility to move freely in a free space 106 arranged at this place in mount 100, which has a substantially annular shape, following an oscillation transverse to the axis, in particular an oscillation in a plane extending perpendicular to this axis at mount 100.

It should be noted that, in addition to the increased compactness, the particular arrangement according to the invention offers the possibility to offset the center of gravity G of inertial mass 26 behind the center of mount 100, increasing accordingly the inertia effect.

Figure 14:
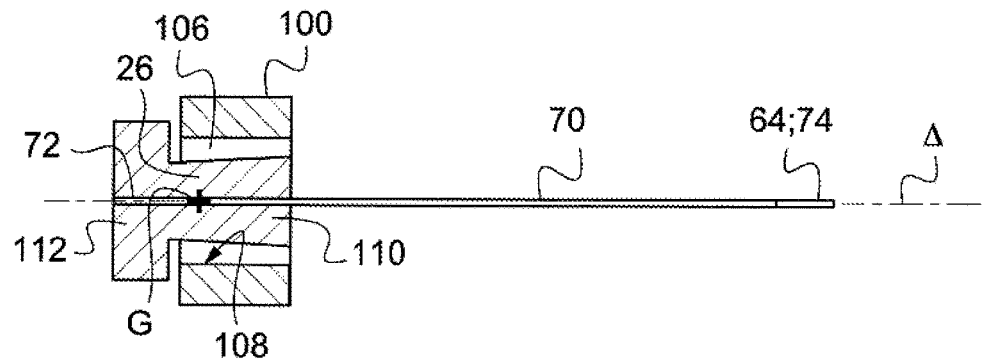
FIG. 14 is a schematic cross-sectional view of the unit of FIG. 13, with a mobile PZT in central position.
Figure 15:
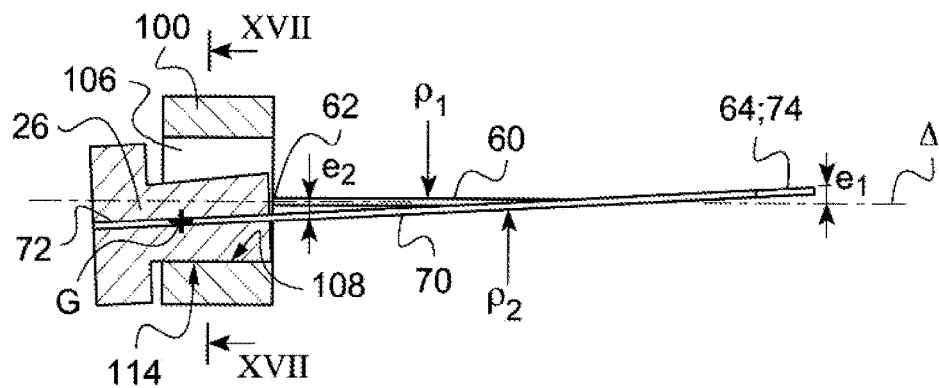
FIG. 15 is similar to FIG. 14, in a configuration of maximum deformation of the PZT with abutment of the inertial mass against an inner surface of the mount.

FIGS. 14 and 15 show in cross-section the unit of FIG. 13, respectively with the PZT stationary in central position (hence in alignment on axis) and in a configuration of maximum deformation. In the latter case, external arms 60 are deformed in a first direction (towards the top of the Figure) with a curvature 1 and an excursion e1 with respect to axis, and internal arms 70 are deformed in the opposite direction with an opposite curvature 2 and a maximum excursion e2 with respect to axis. It will be noted that the total deformation of the PZT corresponds to the sum of both excursions e1 and e2, with the advantage of a significant deformation (|e1|+|e2|) in a relatively small volume of travel, with respect to a conventional PZT configuration such as that illustrated in FIG. 3.

Advantageously, mount 100 includes in the inner volume 106, an inner surface 108 against which a facing outer surface 114 of inertial mass 26 can come into abutment, in order to avoid an excessive deformation of the PZT under heavy stresses and to therefore preserve the longevity of the unit. This abutment, by contact between the inertial mass and the mount, avoids any direct contact with the beam, as is the case in certain known stroke-limitation devices, for example that described by U.S. Pat. No. 10,974,056 B2 (Regnier et al.).

Figure 16:
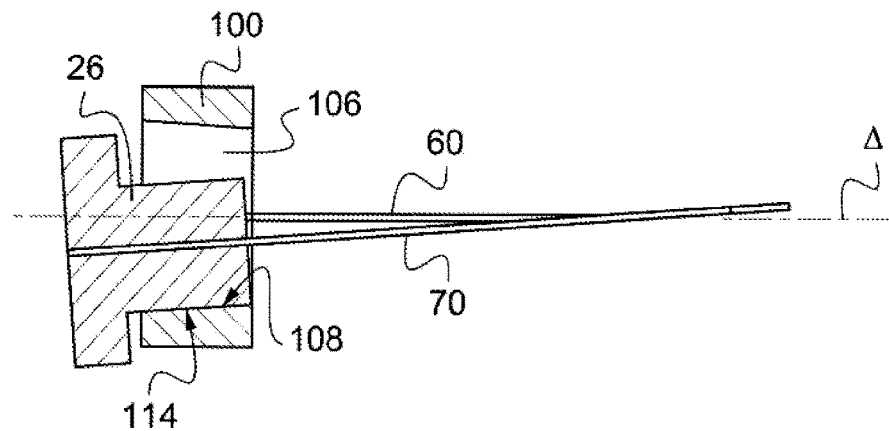
FIG. 16 is similar to FIG. 15, for an alternative in which the inertial mass has a flat outer shape and the counterpart inner abutment surface of the mount is inclined.

FIG. 16 illustrates an alternative of FIG. 15 in which the inner abutment surface 108 of mount 100 is a surface inclined with respect to axis (instead of being parallel to axis as in the case in FIG. 15), and the complementary surface 114 of the inertial mass is a plane surface (instead of being an inclined surface as in the case of FIG. 15).

Figure 17:
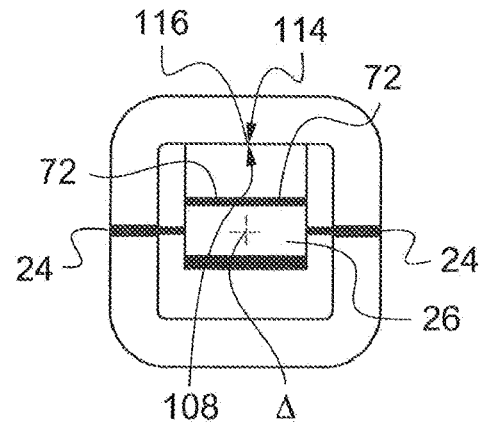
FIG. 17 is a cross-sectional view of the mount of FIG. 16, showing the plane abutment contact of the inertial mass against the counterpart inner surface of the mount.

FIG. 17 is a cross-sectional view of the mount of FIG. 16, showing the cross-sectional contact between the complementary surfaces 108 and 114, which is a plane contact 116 over a relatively large area.

Figure 18:
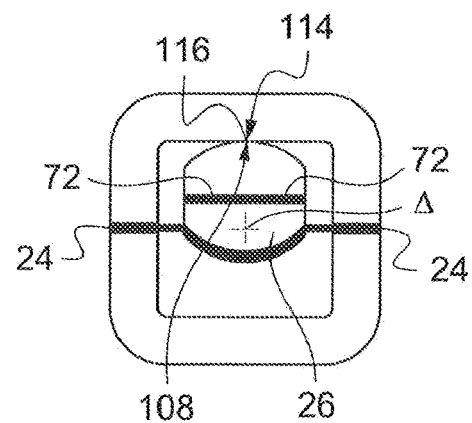
FIG. 18 is similar to FIG. 17, for an alternative in which the abutment contact is an axial linear contact.

In an alternative illustrated in FIG. 18, one of the surfaces 108, 114 is a curved surface and the other a plane surface, and the mutual contact 118 is an axial, linear contact.

Figure 19:
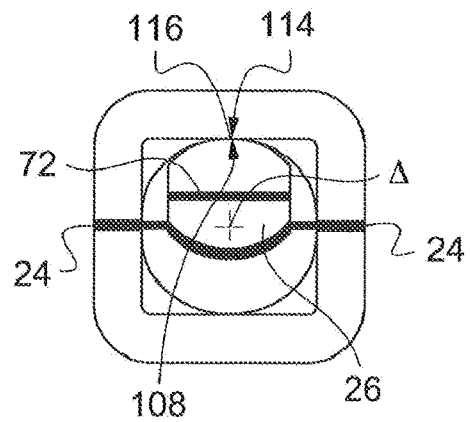
FIG. 19 is similar to FIG. 17, for another alternative in which the abutment contact is a cylindrical surface contact.

In another alternative illustrated in FIG. 19, surfaces 108 and 114 are both curved surfaces, and the contact between these surfaces is a cylindrical surface contact, which provides a better shock absorption due to the largest mutual contact area.

Figure 20:
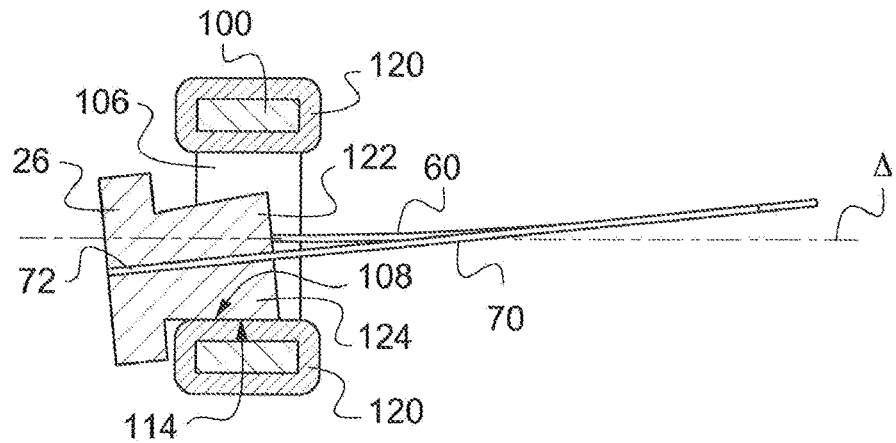
FIG. 20 is similar to FIG. 15, for a contact of the inertial mass against an inner face of the mount coated with a polymer or silicone layer.
Figure 21:
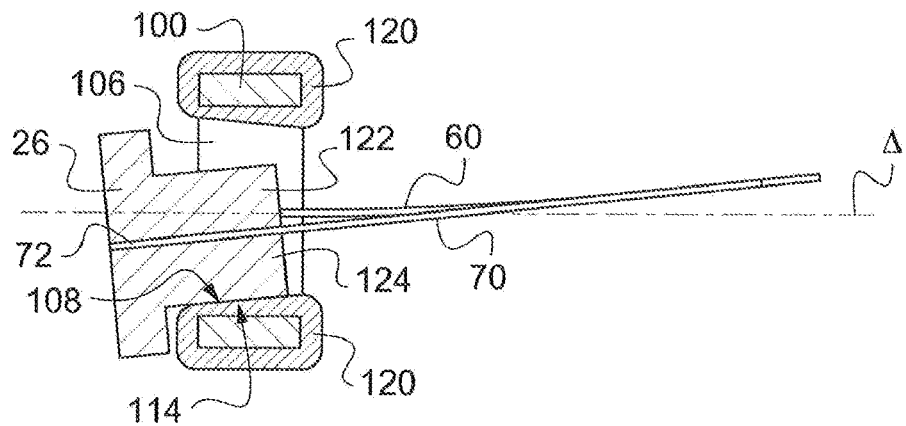
FIG. 21 is similar to FIG. 16, for a contact of the inertial mass against an inner face of the mount coated with a polymer or silicone layer.

FIGS. 20 and 21 are similar to FIGS. 15 and 16, for an alternative in which the contact areas of mount 100 are covered with a suitable shock-absorbing coating, for example a polymer or a silicone, in such a way as to avoid a metal/metal contact between inertial mass 26 and mount 100 as in the previous examples.

Figure 22:
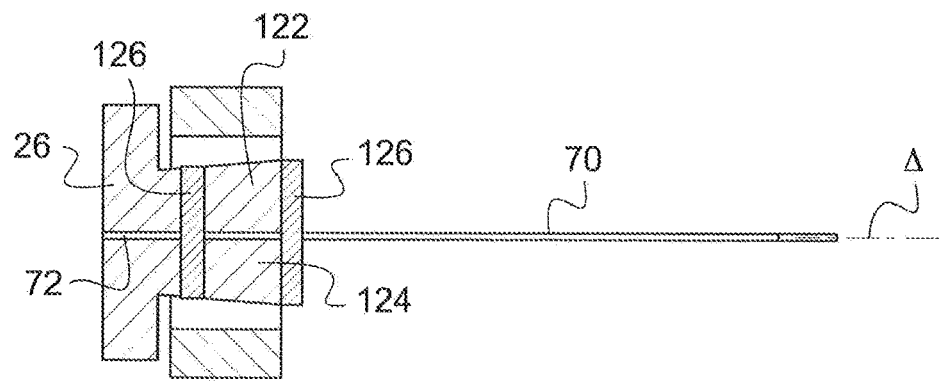
FIG. 22 is similar to FIG. 14, for an alternative in which the mounting of the inertial mass to the beam is a welded mounting, without gluing.

FIG. 22 illustrates a particular way to make the mounting of inertial mass 26 to proximal end 72 of arms 70.

In the preceding examples, for example in FIG. 20, inertial mass 26 is consisted of two distinct parts 122, 124 bonded to end 72 of internal arms 70, this end being sandwiched between parts 122 and 124. Bonding can, however, present a number of difficulties and limitations if flawless reliability of the device is to be guaranteed throughout its lifetime (at least 10 years). For those reasons, a non-bonded construction may be preferable, for example a fully-welded construction such as that illustrated in FIG. 22, where the two parts 124, 126 are joined together by welded pins 126 connecting parts 124, 126 to each other by sandwiching proximal end 72 of internal arms 70.

Various embodiments of the invention implementing an intermediate flyweight 130 ballasting the distal ends of external and internal arms 60, 70 at the place of their junction 80 will now be described with reference to FIGS. 23 to 28.

Figure 26:
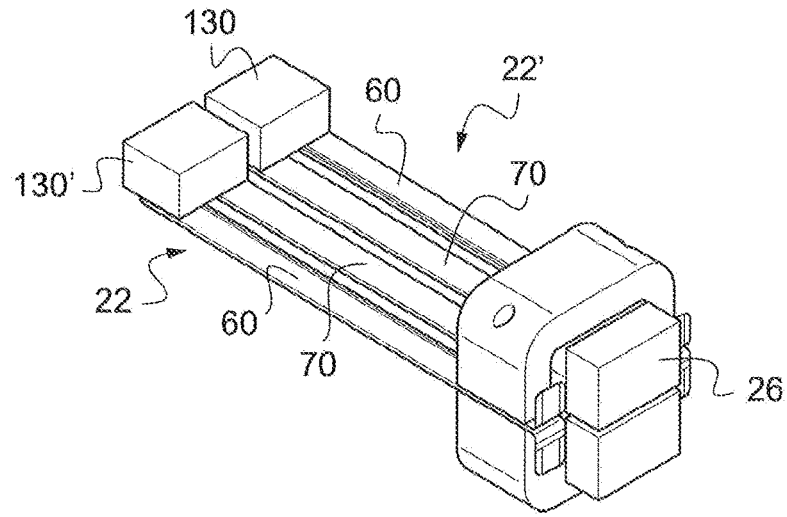
FIG. 26 is similar to FIG. 23, for an alternative in which distinct flyweights are added on one face of the PZT, separately for each of the PZT beams.
Figure 27:
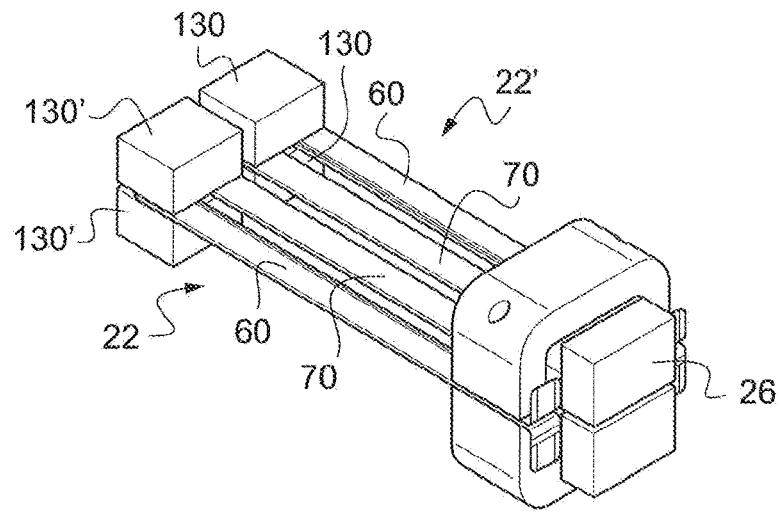
FIG. 27 is similar to FIG. 26, for an alternative in which the flyweights are added on each of the top and bottom faces of the PZT.

The presence of an intermediate flyweight 130 at this place provides several advantages:
- it is a rigid element that relieves the stresses at the junction curvatures 80 between internal 70 and external 60 arms, at a place where these stresses are liable to be particularly heavy;
- the presence of a flyweight 130 at this place has no impact on the conversion efficiency, insofar as it is an area of the beam that produces almost no charge (the bending of the PZT material being minimum at this place, where there is no electrode), and thus no impact on the electrical efficiency of the PEH;
- intermediate flyweight 130 constitutes an additional mobile mass for internal arms 70, which accentuates the pendular oscillation effect for these latter;
- to optimize the production of energy by the transducer, it is possible to dissociate the vibration regimes of the two beams, as will be explained with reference to FIGS. 26 to 28 hereinafter.

Figure 23:
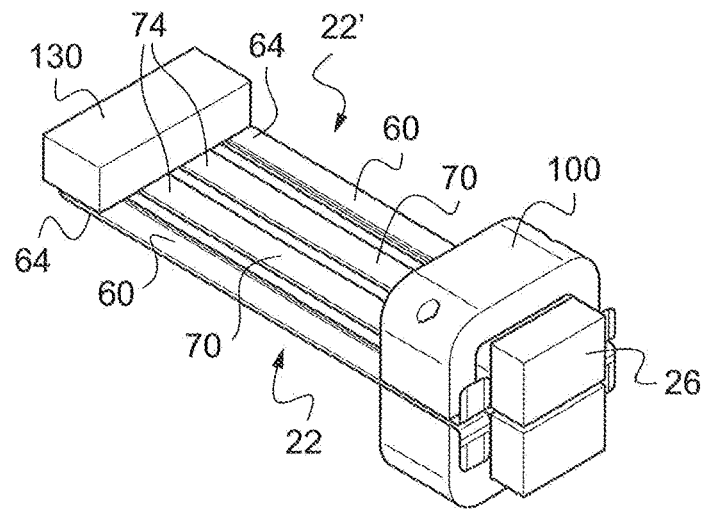
FIG. 23 is similar to FIG. 13, for an embodiment in which an intermediate flyweight is added on one face of the PZT, at the junction between the internal and external arms.

In the alternative of FIG. 23, a single flyweight 130 is arranged, for example bonded, on the top face of the two beams 22, 22' and is common to these two beams.

Figure 24:
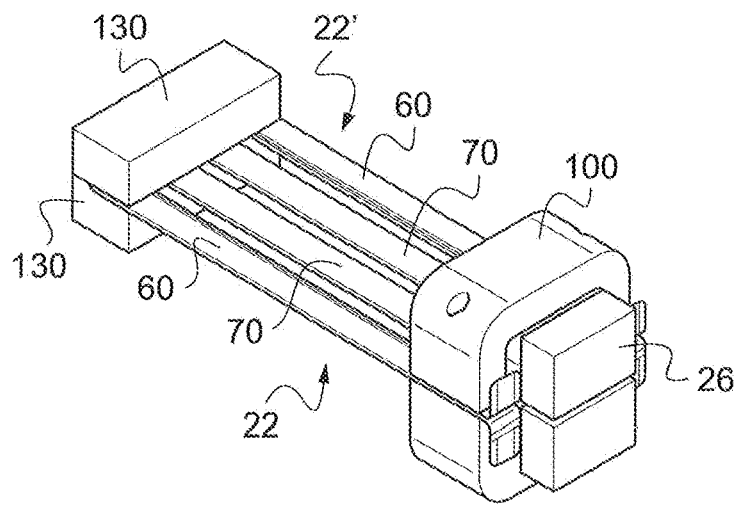
FIG. 24 is similar to FIG. 23, for an alternative in which flyweights are added on each of the top and bottom faces of the PZT.

In the alternative of FIG. 24, a flyweight 130 is mounted on each of the two top and bottom faces of the two beams 22, 22', the flyweights 130 being here again common to the two beams.

Figure 25:
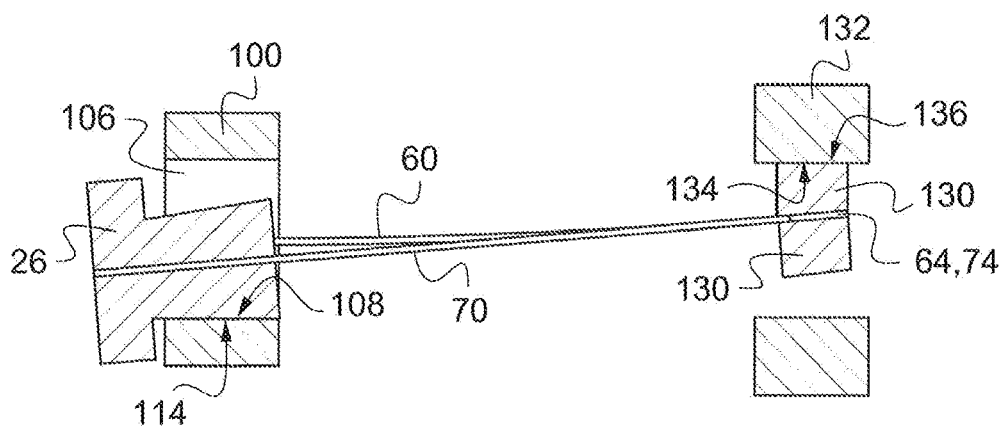
FIG. 25 is a similar cross-sectional view of FIG. 15, for the alternative of FIG. 24.

FIG. 25 is a similar cross-sectional view of FIG. 24, for a configuration of maximum deformation of the PZT. Advantageously, a part 132 makes it possible to limit the maximum deformation on the side of distal ends 64, 74 of arms 60, 70, by abutment against an inner surface 134 of a counterpart outer surface 136 of each of the intermediate flyweights 130. This arrangement ensures a dual limitation of the PZT deformation, on the distal side, by the abutment surfaces 134 of part 132, and on the proximal side, by the abutment surfaces 108 of mount 100, each time without direct contact with the material of the beam.

The alternatives of FIGS. 26 and 27 are similar to those of FIGS. 23 and 24, with intermediate flyweight 130 split into two distinct flyweights 130, 130', each for one the two beams 22, 22'. The two beams are hence not coupled to the distal ends of arms 60, 70, which makes it possible to dissociate their oscillation regime.

Geometries and/or masses and/or densities of intermediate flyweights 130, 130' may be chosen in such a way as to produce different oscillation regimes for each of the two beams 22, 22', to optimize the energy harvesting. Moreover, in addition to intermediate flyweights 130, 130', it is possible to give the two beams different lengths and/or widths to modify the vibration mode thereof, for example different arm lengths as illustrated with beams 22, 22' in FIG. 28.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

The invention claimed is:

1. An energy harvesting module comprising a pendular unit subjected to external stresses applied to the module,
    the pendular unit comprising a piezoelectric transducer extending, along a central axis corresponding to a direction of greater length of the piezoelectric transducer, from a distal end to an opposite proximal end, the piezoelectric transducer being elastically deformable in bending between a clamped end and a free end coupled to an inertial mass,
    the piezoelectric transducer being adapted to convert a mechanical energy produced by oscillations of the pendular unit into an oscillating electrical signal collected by surface electrodes of the piezoelectric transducer,
    wherein the piezoelectric transducer comprises at least one piezoelectric beam configured into two adjacent arms formed single-piece, with an external arm and an internal arm arranged side-by-side,
    wherein the external arm has a proximal end fastened to a clamp and a free distal end, and the internal arm has a free proximal end supporting the inertial mass, and a free distal end connected to the distal end of the external arm,
    wherein the module further comprises, around the central axis, an annular mount that surrounds the piezoelectric beam at its proximal end and that comprises said clamp to which is fastened the proximal end of the external arm,
    and wherein the annular mount includes, in a central region in the vicinity of the clamp, a cavity inside which the inertial mass carried by the free proximal end of the internal arm can oscillate transversely to the central axis.

2. The module of claim 1, wherein the annular mount comprises a stroke limiter having inside the cavity stroke-limiting surfaces adapted to form a stop for the inertial mass in a configuration of maximum bending of the piezoelectric beam.

3. The module of claim 2, wherein the inertial mass comprises stroke-limiting surfaces complementary of the facing stroke-limiting surfaces of the annular mount.

4. The module of claim 3, wherein a mutual contact between the stroke-limiting surfaces of the annular mount and the stroke-limiting surfaces of the inertial mass is one of: a plane contact, a linear contact, or a surface-cylindrical contact.

5. The module of claim 2, wherein the stroke-limiting surfaces of the annular mount and/or of the inertial mass are coated with a flexible damping material, or made of a damping material.

6. The module of claim 1,
wherein the piezoelectric transducer comprises two coplanar piezoelectric beams arranged side-by-side, each of the piezoelectric beams comprising a said external arm and a said internal arm,
wherein the proximal ends of the internal arms of the two piezoelectric beams support together the inertial mass, and
wherein the proximal ends of the external arms of the two piezoelectric beams are each connected to a respective clamp of the annular mount, said respective clamps being both located on either side of the inertial mass in the cavity.

7. The module of claim 1, wherein the position of the center of gravity of the inertial mass is located inside the cavity of the annular mount.

8. The module of claim 1, wherein, in an axial direction of the beam in its longer dimension, the position of the center of gravity of the inertial mass is offset in a proximal direction with respect to the center of the annular mount cavity.

9. The module of claim 1, wherein the piezoelectric beam carries at its free distal end an intermediate flyweight at a junction between the external arm and the internal arm.

10. The module of claim 9, wherein the module further comprises, in the vicinity of the distal end of the piezoelectric beam, a stroke limiter adapted to form a stop for the intermediate flyweight in a configuration of maximum bending of the piezoelectric beam.

11. An autonomous device housing, within a device body:
an electronic unit;
an energy harvesting module outputting an oscillating electric signal;
a power management circuit, adapted to rectify and regulate the oscillating electric signal produced by the energy harvesting module, to output stabilized direct voltage or current; and
an energy storage component for powering the electronic unit,
wherein said stabilized direct voltage or current provided by the power management circuit is used to power the electronic unit and/or to charge the energy storage component of the autonomous device,
wherein the energy harvesting module comprises a pendular unit subjected to external stresses applied to the module,
the pendular unit comprising a piezoelectric transducer extending, along a central axis corresponding to a direction of greater length of the piezoelectric transducer, from a distal end to an opposite proximal end, the piezoelectric transducer being elastically deformable in bending between a clamped end and a free end coupled to an inertial mass,
the piezoelectric transducer being adapted to convert a mechanical energy produced by oscillations of the pendular unit into an oscillating electrical signal collected by surface electrodes of the piezoelectric transducer,
wherein the piezoelectric transducer comprises at least one piezoelectric beam configured into two adjacent arms formed single-piece, with an external arm and an internal arm arranged side-by-side,
wherein the external arm has a proximal end fastened to a clamp and a free distal end, and the internal arm has a free proximal end supporting the inertial mass, and a free distal end connected to the distal end of the external arm,
wherein the module further comprises, around the central axis, an annular mount that surrounds the piezoelectric beam at its proximal end and that comprises said clamp to which is fastened the proximal end of the external arm, and
wherein the annular mount includes, in a central region in the vicinity of the clamp, a cavity inside which the inertial mass carried by the free proximal end of the internal arm can oscillate transversely to the central axis.

12. An active medical device of an implantable autonomous capsule type comprising:
a capsule body with an element for its anchoring to a wall of a patient's organ, wherein external stresses to which is subjected a pendular unit of an energy harvesting module are stresses applied to the capsule body under the effect of movements of said wall and/or blood flow rate variations in a surrounding environment; and
within the capsule body:
an electronic unit;
an energy harvesting module outputting an oscillating electric signal;
a power management circuit, adapted to rectify and regulate the oscillating electric signal produced by the energy harvesting module, to output stabilized direct voltage or current; and
an energy storage component for powering the electronic unit, wherein said stabilized direct voltage or current provided by the power management circuit is used to power the electronic unit and/or to charge the energy storage component of the autonomous device,
wherein the energy harvesting module comprises a pendular unit subjected to external stresses applied to the module,
the pendular unit comprising a piezoelectric transducer extending, along a central axis corresponding to a direction of greater length of the piezoelectric transducer, from a distal end to an opposite proximal end, the piezoelectric transducer being elastically deformable in bending between a clamped end and a free end coupled to an inertial mass,
the piezoelectric transducer being adapted to convert a mechanical energy produced by oscillations of the pendular unit into an oscillating electrical signal collected by surface electrodes of the piezoelectric transducer,
wherein the piezoelectric transducer comprises at least one piezoelectric beam configured into two adjacent arms formed single-piece, with an external arm and an internal arm arranged side-by-side,
wherein the external arm has a proximal end fastened to a clamp and a free distal end, and the internal arm has a free proximal end supporting the inertial mass, and a free distal end connected to the distal end of the external arm,
wherein the module further comprises, around the central axis, an annular mount that surrounds the piezoelectric beam at its proximal end and that comprises said clamp to which is fastened the proximal end of the external arm, and
wherein the annular mount includes, in a central region in the vicinity of the clamp, a cavity inside which the inertial mass carried by the free proximal end of the internal arm can oscillate transversely to the central axis.

* * * * *